(12) United States Patent
Horning et al.

(10) Patent No.: US 8,398,239 B2
(45) Date of Patent: Mar. 19, 2013

(54) WEARABLE EYE TRACKING SYSTEM

(75) Inventors: Robert D. Horning, Savage, MN (US);
Thomas Ohnstein, Roseville, MN (US);
Bernard Fritz, Eagan, MN (US)

(73) Assignee: Honeywell International Inc.,
Morristown, NJ (US)

( * ) Notice: Subject to any disclaimer, the term of this patent is extended or adjusted under 35 U.S.C. 154(b) by 185 days.

(21) Appl. No.: 12/710,941

(22) Filed: Feb. 23, 2010

(65) Prior Publication Data
US 2010/0220291 A1    Sep. 2, 2010

Related U.S. Application Data

(60) Provisional application No. 61/156,633, filed on Mar. 2, 2009.

(51) Int. Cl.
*A61B 3/14* (2006.01)
*A61B 3/10* (2006.01)
(52) U.S. Cl. .................. 351/209; 351/210; 351/221
(58) Field of Classification Search .................. 351/209, 351/210, 221
See application file for complete search history.

(56) References Cited

U.S. PATENT DOCUMENTS

| 5,270,748 A | 12/1993 | Katz |
| 5,861,936 A | 1/1999 | Sorensen |
| 6,299,308 B1 * | 10/2001 | Voronka et al. ............... 351/210 |
| 7,553,021 B2 * | 6/2009 | Fergason et al. .............. 351/210 |
| 2005/0195277 A1 | 9/2005 | Yamasaki | |

FOREIGN PATENT DOCUMENTS

| EP | 0590231 A2 | 4/1994 |
| WO | 2007097738 A2 | 8/2007 |

OTHER PUBLICATIONS

EP Communication for 10 155 078.8 dated Aug. 21, 2012.
EP Search Report for 10 155 078.8 dated Aug. 9, 2012.
Israel Office Action for IL 204241 dated Dec. 19, 2012.

* cited by examiner

*Primary Examiner* — Jack Dinh
(74) *Attorney, Agent, or Firm* — Ingrassia Fisher & Lorenz, P.C.

(57) ABSTRACT

An eye tracking system includes a transparent lens, at least one light source, and a plurality of light detectors. The transparent lens is adapted for disposal adjacent an eye. The at least one light source is disposed within the transparent lens and is configured to emit light toward the eye. The at least one light source is transparent to visible light. The plurality of light detectors is disposed within the transparent lens and is configured to receive light that is emitted from the at least one light source and is reflected off of the eye. Each of the light detectors is transparent to visible light and is configured, upon receipt of light that is reflected off of the eye, to supply an output signal.

19 Claims, 2 Drawing Sheets

WEARABLE EYE TRACKING SYSTEM

PRIORITY CLAIMS

This application claims the benefit of U.S. Provisional Application No. 61/156,633 filed Mar. 2, 2009.

TECHNICAL FIELD

The present invention generally relates to eye tracking systems and methods, and more particularly relates to a wearable eye tracking system and method that does not rely on relatively bulky devices.

BACKGROUND

Eye tracking systems are used in various systems to implement various functions. Some examples of the functions that eye tracking systems implement include touch-free control of a cursor on a display, control of an apparatus in an aircraft cockpit or other vehicle, diagnostics and monitoring, and training/system simulation. A typical eye tracking system may include a suitable light source and a camera. The light source illuminates the face of a user, and the camera detects two reflections from one of the user's eye. The first reflection is from the front surface of the cornea. The second reflection is from the retina, and it illuminates the iris of the eye. Processing circuitry, using relatively straightforward geometrical calculations based on these two reflections, computes the direction in which the eye is gazing.

Conventional eye tracking systems may be generally categorized as desktop systems and wearable systems. Desktop systems rest on a surface and track the eye movement of a user that is facing the system, whereas wearable systems may be mounted on a pair of glasses and worn by the user. Both categories of presently known eye tracking systems do suffer certain drawbacks. For example, desktop systems typically have a relatively small depth of field and field of view. Moreover, many desktop systems may be inordinately large, may prevent portability, and may rely on a limited range of head motion. Wearable systems can be relatively clumsy and bulky, and may lack sufficient ruggedness. Furthermore, both system categories presently implement extensive computation for image analysis of the face and eye, both may work poorly in bright indoor or outdoor lighting, both may implement extensive computation to determine the gaze direction.

Hence, there is a need for an eye tracking system that is both wearable and overcomes at least the above-note shortcomings of presently known eye tracking systems. The present invention addresses at least this need.

BRIEF SUMMARY

In one exemplary embodiment, an eye tracking system includes a transparent lens, at least one light source, and a plurality of light detectors. The transparent lens is adapted for disposal adjacent an eye. The at least one light source is disposed within the transparent lens and is configured to emit light toward the eye. The at least one light source is transparent to visible light. The plurality of light detectors is disposed within the transparent lens and is configured to receive light that is emitted from the at least one light source and is reflected off of the eye. Each of the light detectors is transparent to visible light and is configured, upon receipt of light that is reflected off of the eye, to supply an output signal.

In another exemplary embodiment, an eye tracking system includes a frame, a first transparent lens, a second transparent lens, a first light source, and a plurality of first light detectors. The frame is configured to be worn on a head of a user, and includes a frame front, a first temple, and a second temple. The frame front has a first lens opening and a second lens opening. The first and second temples are each coupled to the frame front and are configured to rest on an ear of the user. The first transparent lens is disposed within the first lens opening. The second transparent lens disposed within the second lens opening. A first light source is coupled to the frame and is configured to emit light toward a first eye of the user. The plurality of first light detectors is disposed within the first transparent lens and is configured to receive light that is emitted from the first light source and is reflected off of the first eye. Each of the light detectors is transparent to visible light and is configured, upon receipt of light that is reflected off of the first eye, to supply a first output signal.

Furthermore, other desirable features and characteristics of the eye tracking system will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Figure 1:
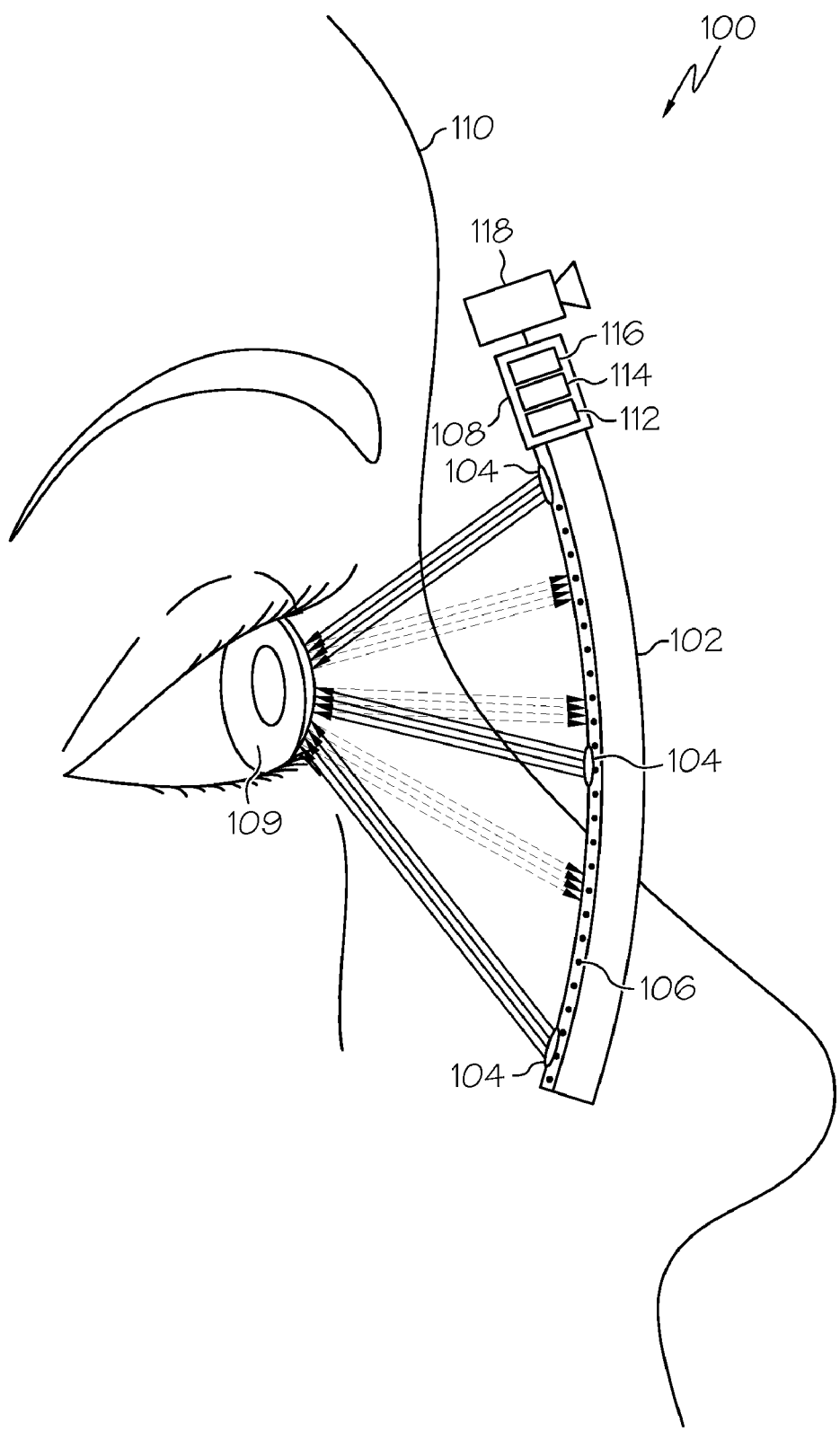
FIG. 1 depicts a functional block diagram of one embodiment of an eye tracking system.

Referring first to FIG. 1, a block diagram of one embodiment of an eye tracking system 100 is depicted and will be described. The depicted system 100 includes a lens 102, a plurality of light sources 104, a plurality of light detectors 106, and processing circuitry 108. The lens 102 is adapted to be disposed adjacent to the eye 109 of a user 110. In a particular preferred embodiment, as will be described further below, the lens 102 is coupled to a glasses frame. Preferably, a reflective coating is disposed on the outer surface of the lens 102 to reflect light at or near the wavelength of the light emitted by the light sources 104. The lens 102 may additionally include a suitable coating or filter in front of (or over) the light detectors 106 to filter out all light except for wavelengths at or near the detection wavelength of the light detectors 106.

The light sources 104 are preferably disposed within the lens 102, and are configured to emit light toward the eye 109 of the user 110. Although the light sources 104 are, for illustrative purposes, visible in FIG. 1, the light sources 104 are preferably formed of transparent electronics. As is generally known, transparent electronics may be formed of organic materials, ZnO, GaN, or other materials, and are transparent to light in the visible spectrum. Thus, when disposed within the lens 102, the light sources 104 will not be visible to the eye 109. It will be appreciated, however, that in some embodiments one or more of the light sources 104 may be mounted on wearable headgear, such as a glasses frame, which is described further below.

It will additionally be appreciated that the light sources 104 may be comprised any one of numerous types of light sources. For example, in one embodiment the light sources 104 comprise LEDs that emit at least partially collimated light, and in another embodiment the light sources 104 comprise lasers. No matter the specific implementation, the light sources 104 preferably emit light in a near infrared wavelength such as, for example, about 880 nm. Although a plurality of light sources 104 is depicted in FIG. 1, it will be appreciated that the system 100 could be implemented using a single light source 104.

The light detectors 106 are also preferably disposed within the lens 102, and each light detector 106 is configured to receive light is that reflected off of the eye 109. Similar to the light sources 104, each of the light detectors 106 is preferably formed of transparent electronics. Thus, the light detectors 106 are transparent to visible light, yet sensitive to the light emitted by the light sources 104. Also consistent with the description of the light sources 104, it will be appreciated that the number and type of light detectors 106 may vary. In one particular embodiment, the light detectors 106 are each implemented as photodiodes. No matter the number and type of light detectors 106, each is configured, upon receipt of light that is reflected off of the eye 109, to supply an output signal to the processing circuitry 108.

Figure 2:
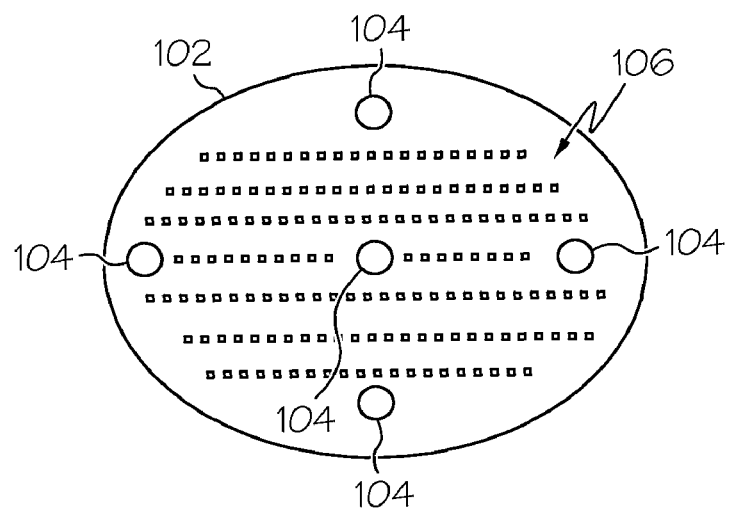
FIG. 2 depicts a simplified schematic representation of a lens that may be used in the exemplary system of FIG. 1.

Before proceeding further, it is noted that not only may the number and type of light sources 104 and light detectors 106 vary, but the particular layout of the light sources 104 and light detectors 106 within the lens 102 may also vary. For example, FIG. 2 depicts one embodiment of a lens 102 that has a plurality of light sources 104 and light detectors 106 disposed therein. In this embodiment, the light sources 104 are position in a cross pattern, however, in other embodiments various other patterns may be used. The light detectors 106 are depicted as being positioned in a two-dimensional array across the lens 102. It will be appreciated that the depicted orderly two-dimensional array of rows and columns is merely exemplary, and that in other embodiments the light detectors 106 may be positioned in various other two-dimensional patterns or in a random manner.

Returning to FIG. 1, the processing circuitry 108 is coupled to the light sources 104 and to the light detectors 106. The processing circuitry 108 is preferably configured to control light emission from the light sources 104, and to receive the output signals supplied from each of the light detectors 106. The processing circuitry 108 is further configured, in response the output signals from the light detectors 106, to determine a gaze direction of the eye 109. The processing circuitry 108 may be variously configured to implement its functionality. For example, in some embodiments the processing circuitry 108 is entirely disposed within the lens 102 and is thus comprised wholly of transparent electronics. In other embodiments, only portions of the processing circuitry 108 may be disposed within the lens 102, while other portions are disposed on or within other structure, such as the glasses frame that is described further below. In these latter embodiments, a radio frequency (RF) link may be used to transmit data to those portions of the processing circuitry 108 disposed on or within other structure, thereby eliminating the need for physical wires.

In one particular preferred embodiment, the processing circuitry 108 includes neuromorphic circuitry 112 and a processor 114, both of which are preferably energized via a suitable power source 116, such as a battery. The neuromorphic circuitry 112 preferably comprises transparent electronics and, though not depicted as such in FIG. 1, is preferably disposed within the lens 102. As is generally known, neuromorphic circuitry 112 exhibits inherent edge and motion detection, which reduces computation and power consumption, thereby allowing for a relatively smaller and lower-power processor 114. The neuromorphic circuitry 112 also ignores non-moving or uninteresting output from the light detectors 104, is 10-100 times faster than digital imaging circuitry, and exhibits 10-100 times greater dynamic range than digital imaging circuitry.

The neuromorphic circuitry 112 receives the output signals from the light detectors 104 and supplies signals to the processor 114. The processor 114 is configured, in response to the signals supplied from the neuromorphic circuitry 112, to determine the gaze direction of the eye 109. In particular, as FIG. 1 depicts the light sources 104 each emit light toward the eye 109 of the user 110, which is in turn reflected off of the eye 109 at an angle based on the orientation (i.e., gaze direction) of the eye 109 relative to each light source 104. Thus, as the eye 109 moves, the location at which the reflected light from each light source 104 hits the light detectors 106 changes. In one embodiment, the processing circuitry 108 processes the change in light detection of particular light detectors 106. In another embodiment, the processing circuitry 108 compares the current state of each light detector 106 to past states and/or directly computes the gaze direction based on the current state.

In some embodiments, gaze direction is determined based solely on light reflections off of the front surface (cornea) of the eye 109. In other embodiments, the gaze direction is determined based on light reflections off of both the cornea of eye 109 and the retina of eye 109. To determine the gaze direction based on reflections off the cornea of the eye 109, the differences in location of the reflected light sensed by the light detectors 106 are used. The differences in location of the reflected light are caused by the shape of the cornea of eye 109. The cornea of an eye forms a bulge on the eye 109, which causes light to reflect off the eye at different angles depending on the gazed direction relative to the light sources 104. The difference in angle of the reflections off of the eye 109 causes the reflections to be sensed by different light detectors 106 depending on the gaze direction of the eye 109. Thus, the gaze direction of the eye 109 may be determined based on which light detectors 106 sense reflections.

As was previously noted, the processing circuitry 108 is also configured to control light emission from the light sources 104. In some embodiments, each light source 104 is configured and controlled to emit a unique pattern or pulse of light. In such embodiments, the processing circuitry 108 is configured to distinguish the reflected light received by each light detector 106 based on the unique pattern or pulse. In other words, the processing circuitry 108 may match light received by one or more light detectors 106 to a particular one of the light sources 104. As a result, the reflection location of each individual light source 104 may be distinguished from other light sources 104 and used to determine the gaze direction of the eye 109. In these embodiments, the processing circuitry 108 may implement a phase locked loop (PLL) circuit to discriminate between reflections of light from the light sources 104 and stray light that is detected by the light detectors 106. In one embodiment, the PLL circuit distinguishes between light sources 104 by locking on to a specific frequency of a pulse from a particular light source 104 to distinguish that particular light source 104 from other light sources.

As FIG. 1 additionally depicts, the system 100 may, at least in some embodiments, be implemented with an outward facing camera 118. In such embodiments, the camera 118 is coupled to, and controlled by, the processing circuitry 108 to follow the movement of the eye 109. More specifically, processing circuitry 108 is configured to control the view of the camera 118 in a manner that that the camera 118 captures images of the scene in the gaze direction of the eye 109.

Figure 3:
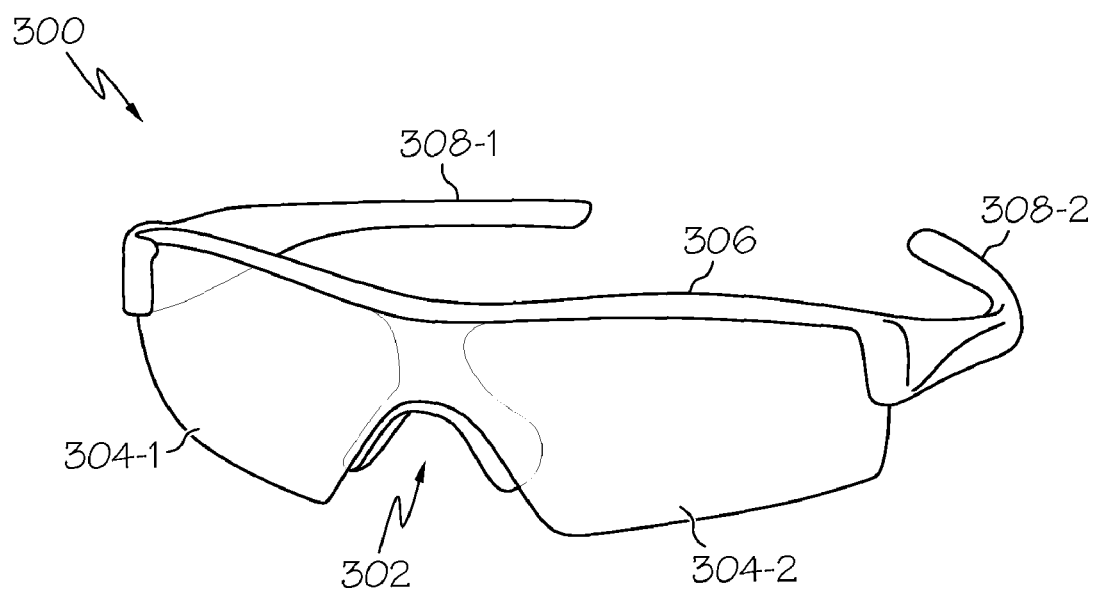
FIG. 3 depicts a simplified representation of the exemplary system of FIG. 1 implemented in a pair of glasses to be worn by a user.

It was noted above that the system 100 may, at least in some embodiments, be integrated into a pair of eye glasses 300. One such embodiment is depicted in FIG. 3, which depicts a frame 302 and two lenses—a first lens 304-1 and a second lens 304-2. The frame 302 may be configured like any one of numerous conventionally known glasses frames that may be worn by a user 110. In the depicted embodiment the frame 302 includes a frame front 306, a first temple 308-1, and a second temple 308-2. The first and second temples 308-1, 308-2 are each coupled to and extend from the frame front 306, and are each configured to rest on an ear of a user 110.

The first and second lenses 304-1, 304-2 are each coupled to the frame front 306 and, when the glasses 300 are worn by a user 110, are disposed adjacent the eyes 109 of the user 110. For example, in one embodiment, the glasses 300 are configures so that the lenses 304-1, 304-2 are from about 1 to 5 centimeters away from the eye 109 of a user 110. Although the first and second lenses 304-1, 304-2 are depicted in FIG. 3 as being integrally formed, it will be appreciated that in other embodiments the lenses 304-1, 304-2 could be physically separate from each other.

Whether or not the lenses 304-1, 304-2 are integral or separate, one or both of the lenses 304-1, 304-2 may be configured similar to the lens 102 depicted in FIG. 1, and thus include light sources 104, light detectors 106, and some or all of the processing circuitry 108 described above. For those embodiments in which both lenses 304-1, 304-2 are configured similar to the lens 102 of FIG. 1, the system 100 is preferably configured to detect the gaze direction of both eyes 109 of the user 110. The processing circuitry 108 may be configured to average, or otherwise combine, the gaze direction of each eye 109 to determine the gaze direction of the user 110. The processing circuitry 108 may also be configured to determine not only the gaze direction, but the distance at which the user is focused. The distance may then be used to focus the camera 118 on the location being observed by the user 110.

As mentioned above, the gaze direction of a user 110 may be used to, for example, control a cursor on a computer screen. The cursor control may then used for specific applications such as data analysis, intelligence, and automation and control. The determined gaze direction may be also be used to operate controls with a relatively faster response than a human hand or foot. This may be useful in a cockpit of an aircraft or in a vehicle for applications such as flight control, visual point-and-shoot, and/or remote control. Additionally, the gaze direction may be used for training or simulation, medical and/or psychological diagnostics and monitoring, or safety and security systems.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An eye tracking system, comprising:
    a transparent lens adapted for disposal adjacent an eye;
    at least one light source disposed within the transparent lens and configured to emit light toward the eye, the at least one light source transparent to visible light; and
    a plurality of light detectors disposed within the transparent lens and configured to receive light that is emitted from the at least one light source and is reflected off of the eye, each of the light detectors transparent to visible light and configured, upon receipt of light that is reflected off of the eye, to supply an output signal.

2. The system of claim 1, further comprising:
    processing circuitry coupled to the at least one light source and each of the light detectors, the processing circuitry coupled to receive the output signals supplied from each of the light detectors and configured, in response thereto, to determine a gaze direction of the eye.

3. The system of claim 2, wherein:
    at least a portion of the processing circuitry is transparent to visible light; and
    that portion of the processing circuitry that is transparent to visible light is disposed within the transparent lens.

4. The system of claim 2, wherein the processing circuitry comprises neuromorphic circuitry.

5. The system of claim 2, wherein the processing circuitry is further configured to supply a gaze direction output signal representative of the determined gaze direction, and wherein the system further comprises:
    a camera coupled to receive the gaze direction output signal and configured, in response thereto, to capture images of a scene in the determined gaze direction.

6. The system of claim 1, wherein the at least one light source is configured to emit near infrared wavelength light.

7. The system of claim 1, wherein the at least one light source is configured to emit at least partially collimated light.

8. The system of claim 1, wherein the at least one light source comprises an organic light emitting diode (OLED).

9. The system of claim 1, wherein the at least one light source comprises a laser.

10. The system of claim 1, wherein each of the light detectors comprises an organic photodetector.

11. An eye tracking system, comprising:
    a frame configured to be worn on a head of a user, the frame including a frame front, a first temple, and a second temple, the first and second temples each coupled to the frame front and configured to rest on an ear of the user;
    a first transparent lens coupled to the frame front;
    a second transparent lens coupled to the frame front;
    a first light source disposed within the first transparent lens and configured to emit light toward a first eye of the user, the first light source is transparent to visible light; and
    a plurality of first light detectors disposed within the first transparent lens and configured to receive light that is emitted from the first light source and is reflected off of the first eye, each of the light detectors transparent to visible light and configured, upon receipt of light that is reflected off of the first eye, to supply a first output signal.

12. The system of claim 11, further comprising:
    processing circuitry coupled to the first light source and each of the first light detectors, the processing circuitry coupled to receive the first output signals supplied from each of the first light detectors and configured, in response thereto, to determine a gaze direction of the first eye.

13. The system of claim 12, wherein:
at least a portion of the processing circuitry is transparent to visible light; and
that portion of the processing circuitry that is transparent to visible light is disposed within the transparent lens.

14. The system of claim 12, wherein at least a portion of the processing circuitry is disposed within the frame.

15. The system of claim 12, wherein the processing circuitry comprises neuromorphic circuitry.

16. The system of claim 12, wherein the processing circuitry is further configured to supply a gaze direction output signal representative of the determined gaze direction, and wherein the system further comprises:
a camera coupled to the frame, the camera coupled to receive the gaze direction output signal and configured, in response thereto, to capture images of a scene in the determined gaze direction.

17. The system of claim 11, further comprising:
a second light source disposed within the second transparent lens and configured to emit light toward a second eye of the user, the second light source transparent to visible light; and
a plurality of second light detectors disposed with the second transparent lens and configured to receive light that is emitted from the second light source and is reflected off of the second eye, each of the light detectors transparent to visible light and configured, upon receipt of light that is reflected off of the second eye, to supply a second output signal 18. The system of claim 17, further comprising:
processing circuitry coupled to the first light source, the second light source, the first light detectors, and the second light detectors, the processing circuitry coupled to receive the first and second output signals supplied from each of the first and second light detectors and configured, in response thereto, to determine a gaze direction of the first eye and the second eye.

19. The system of claim 18, wherein the processing circuitry is further configured to supply a gaze direction output signal representative of the determined gaze direction of the first and second eyes, and wherein the system further comprises:
a camera coupled to the frame, the camera coupled to receive the gaze direction output signal and configured, in response thereto, to capture images of a scene in the determined gaze direction.

* * * * *